(12) United States Patent
Nielsen et al.

(10) Patent No.: US 6,284,292 B1
(45) Date of Patent: *Sep. 4, 2001

(54) METHOD OF ISOLATING PROTEINS

(75) Inventors: Per Munk Nielsen, Hillerod; Ole Regnar Hansen, Herlev, both of (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/265,109

(22) Filed: Mar. 9, 1999

Related U.S. Application Data

(63) Continuation of application No. PCT/DK97/00351, filed on Aug. 28, 1997.

(30) Foreign Application Priority Data

Sep. 16, 1996 (DK) .................................................... 0994/96

(51) Int. Cl.[7] ........................................................ A23L 1/20
(52) U.S. Cl. ................................ 426/46; 426/44; 426/52; 426/656
(58) Field of Search .................................. 426/44, 45, 46, 426/49, 50, 52, 656, 634

(56) References Cited

U.S. PATENT DOCUMENTS

| 3,958,015 | 5/1976 | Gay . |
| 4,420,425 | 12/1983 | Lawhon . |
| 4,478,856 | 10/1984 | Adler-Nissen et al. . |
| 4,478,940 | * 10/1984 | Adler-Nissen et al. ............. 435/209 |
| 5,086,166 | 2/1992 | Lawhon et al. . |

FOREIGN PATENT DOCUMENTS

| 0 370 163 | 5/1990 | (EP) . |
| 2 176 487 | 12/1986 | (GB) . |

OTHER PUBLICATIONS

Lawhon et al., JAOCS, pp. 377–384 (Mar. 1981).

Lawhon et al., Combining Aqueous Extraction and Membrane Isolation Techniques to Recover Protein and Oil from Soybeans, Journal of Food Science, 1981, 46(3), 912–916 & 919.

* cited by examiner

Primary Examiner—Leslie Wong
(74) Attorney, Agent, or Firm—Elias J. Lambiris; Jason I. Garbell

(57) ABSTRACT

The present invention relates to a method of isolating proteins from a proteinaceous vegetable material. More specifically the invention provides a method for isolating proteins from a proteinaceous vegetable material, which method involves the steps of subjecting the proteinaceous vegetable material to the action of one or more carbohydrate degrading enzyme(s), thereby obtaining a mixture comprising proteins and hydrolyzed carbohydrates; and subjecting the mixture of step (i) to a separation process in order to separate the proteins from the hydrolyzed carbohydrates.

30 Claims, No Drawings

METHOD OF ISOLATING PROTEINS

CROSS-REFERENCE TO RELATED APPLICATIONS

This application is a continuation application of PCT/DK97/00351 filed Aug. 28, 1997 and claims priority under 35 U.S.C. 119 of Danish application 0994/96 filed Sep. 16, 1996, the contents of which are fully incorporated herein by reference.

FIELD OF THE INVENTION

The present invention relates to a method of isolating proteins from a proteinaceous vegetable material. More specifically the invention provides a method for isolating proteins from a proteinaceous vegetable material, which method comprises the steps of subjecting the proteinaceous vegetable material to the action of one or more carbohydrate degrading enzyme(s), thereby obtaining a mixture comprising proteins and hydrolyzed carbohydrates; and subjecting the mixture of step (i) to a separation process in order to separate proteins from the hydrolyzed carbohydrates.

BACKGROUND ART

Protein isolates are products of native, unhydrolyzed proteins, obtained by isolating proteins from a proteinaceous source, usually a proteinaceous vegetable source. Protein isolates are also referred to as protein concentrates or purified protein products. Protein isolates find various industrial utility, primarily in the food industry, e.g., for human and animal nutrition, especially products for human infants and young animals.

Methods of producing protein isolates by use of various hydrocarbon specific enzymes have been described. Thus, U.S. Pat. No. 4,478,856 describes a method for producing purified vegetable proteins, and U.S. Pat. No. 3,958,015 describes a method for concentrating soy proteins.

Protein isolates may also be produced by combining aqueous extraction and membrane isolation techniques. Such methods are described by e.g. Lawhon et al. [cf. e.g. Lawhon J T, Rhee K C & Lusas E W; *The Journal of the American Oil chemists Society* 1981 58 (3) 377–384; and Lawhon J T, Manak L J, Rhee K C, Rhee K S & Lusas E W; *Journal of Food Science* 1981 46 (3) 912–916+919]. Also U.S. Pat. No. 4,420,425 and U.S. Pat. No. 5,086,166 describe methods of processing oilseeds comprising solubilizing the proteins and separating the protein fraction by use of an ultrafiltration membrane.

By use of membrane isolation techniques, proteins are recovered from accompanying byproducts, in particular polysaccharides.

Methods of producing protein isolates by the combined action of carbohydrate degrading enzymes and separation techniques have never been described.

SUMMARY OF THE INVENTION

According to the invention it has now been found that the process of isolating vegetable proteins by separation techniques proceeds more efficiently and leads to products of improved quality if the vegetable proteinaceous material is subjected to the action of one or more carbohydrate degrading enzymes.

Accordingly the invention provides a method of isolating proteins from a proteinaceous vegetable material, which method comprises the steps of:

(i) subjecting the proteinaceous vegetable material to the action of one or more carbohydrate degrading enzyme(s), thereby obtaining a mixture comprising proteins and hydrolyzed carbohydrates; and (ii) subjecting the mixture of step (i) to a separation process in order to separate the proteins from the hydrolyzed carbohydrates.

DETAILED DISCLOSURE OF THE INVENTION

The present invention provides a method of isolating proteins from a proteinaceous vegetable material, which method comprises the steps of subjecting the proteinaceous vegetable material to the action of one or more carbohydrate degrading enzyme(s), thereby obtaining a mixture comprising proteins and hydrolyzed carbohydrates, and subjecting the mixture to a separation process in order to separate the proteins from the hydrolyzed carbohydrates.

By the addition of carbohydrate degrading enzymes, the accompanying polysaccharides, which constitute a majority of the byproducts, are hydrolyzed into smaller fragments, thereby increasing differences in size between the main product (the proteins) and the byproducts. The enzyme treatment step according to the invention therefore increases the efficiency of the separation step. During the separation step, solutions having a higher dry matter content can be processed, and the quality of the products becomes improved, in particular with respect to purity and organoleptic properties, i.e. lack of undesirable flavor, odor, and color.

Protein Isolates

The product of the process of this invention is usually referred to as a protein isolate, a protein concentrate or a purified protein product. The proteins essentially are native proteins, that have not become hydrolyzed during the process, and that are not enzymatically modified proteins.

The proteins constitute more than 80% by weight of the dry matter content of the protein isolate obtained by the process of the invention, preferably more than 90% by weight.

The proteins isolated by the method of the invention are particularly useful for incorporation into food products.

Proteinaceous Vegetable Materials

The proteinaceous vegetable material subjected to the method of the invention may be any protein containing material of vegetable sources, and materials obtained therefrom. Preferably the vegetable proteinaceous material is a cereal, maize, rice, sorghum, wheat, soybean, faba bean, cowpeas, cassava, sesame, peanuts, peas, cofton, oilseed, and yams. The vegetable proteinaceous material may be derived from a vegetable source or vegetable material, e.g., by milling, crushing or grounding, such as flour, de-fatted soybean or soybean flakes.

Preferably the proteinaceous vegetable material is essentially free of fibers.

Carbohydrate Degrading Enzymes

The process of the invention comprises subjecting the proteinaceous vegetable material to the action of one or more carbohydrate degrading enzyme(s).

In a preferred embodiment one or more of the enzymes employed in the process is a glycosidase enzyme (EC 3.2).

In a more preferred embodiment one or more of the enzymes employed in the process is an amylase, in particular an α-amylase or a β-amylase, an arabinanase, an arabinofuranosidase, a galactanase, an α-galactosidase, a βgalactosidase, a polygalacturonase, a pectin methyl esterase, a rhamnogalacturonase, a rhamnogalacturon acetyl esterase, a pectin lyase, a xylanase, a cellulase, a β-glucosidase, a cellobiohydrolase, a xylosidase, a mannanase, and/or a glucuronisidase.

In order to obtain an isolate of native proteins, the enzyme preparation should be substantially free of proteolytic enzymes, as these will degrade the protein in question, thereby turning this into a modified protein.

Microbial Sources

The glycosidase enzyme of the invention may be obtained from any known source. Preferably the glycosidase enzyme may be obtained from microbial sources, in particular from a filamentous fungus or a yeast, or from a bacteria.

In particular the amylase may be derived from a strain of Acremonium, a strain of Alcaligenes, in particular *Alcaligenes latus,* a strain of Aspergillus, in particular *Aspergillus kawachii* and *Aspergillus oryzae,* a strain of Bacillus, in particular *Bacillus amyloliquefaciens, Bacillus licheniformis, Bacillus polymyxa, Bacillus subtilis* and *Bacillus stearothermophilus,* a strain of Desulfurococcus, in particular *Desulfurococcus mucosus,* a strain of Fervidobacterium, a strain of Lactobacillus, a strain of Micrococcus, a strain of Pseudomonas, in particular *Pseudomonas amyloderamosa,* a strain of Pyrococcus, in particular *Pyrococcus furiosus* and *Pyrococcus woesei,* a strain of Pyrodictium, a strain of Sulfolobus, a strain of Staphylothermus, or a strain of Thermococcus.

The arabinanase may be derived from a strain of *Aspergillus aculeatus.*

The galactanase may be derived from a strain of Aspergillus in particular *Aspergillus aculeatus,* a strain of Humicola, in particular *Humicola insolens,* a strain of Myceliophthora, in particular *Myceliophthora thermophila,* or a strain of Meripilus, in particular *Meripilus giganteus.*

The galactosidase enzyme (α-galactosidase or β-galactosidase) may be of bacterial origin and derived from a strain of *Escherichia coli,* or a strain of Bacillus, in particular *Bacillus stearothermophilus* and *Bacillus subtilis,* or it may be of fungal origin and derived from a strain of Aspergillus, in particular *Aspergillus aculeatus, Aspergillus ficuum, Aspergillus niger* and *Aspergillus oryzae,* a strain of Klebsiella, in particular *Klebsiella planticola,* a strain of Neurospora, or a strain of Rhizopus, or it may be derived from a yeast, preferably a strain of Saccharomyces, in particular *Saccharomyces cereviciae* and *Saccharomyces oleaginosus.*

The polygalacturonase enzyme may be derived from a strain of Aspergillus, in particular *Aspergillus aculeatus* and *Aspergillus niger,* or a strain of Erwinia, in particular *Erwinia carotovora.*

The pectin methyl esterase enzyme may be derived from a strain of Aspergillus, in particular *Aspergillus aculeatus.*

The rhamnogalacturonase enzyme may be derived from a strain of Aspergillus, in particular a strain of *Aspergillus aculeatus, Aspergillus japonicus,* or from a strain of Irpex, in particular *Irpex lacteus.*

The rhamnogalacturon acetyl esterase enzyme may be derived from a strain of Aspergillus, in particular *Aspergillus aculeatus.*

The xylanase enzyme may of fungal origin and may be derived from a strain of Aspergillus, in particular *Aspergillus aculeatus, Aspergillus awamori, Aspergillus kawachii, Aspergillus nidulans, Aspergillus niger and Aspergillus tubigensis,* a strain of Aureobasidium, a strain of Chaetomium, in particular *Chaetomium gracile,* a strain of Cochliobolus, in particular *Cochliobolus carbonum,* a strain of Disporotrichum, in particular *Disporotrichum dimorphosporum,* a strain of Humicola, in particular *Humicola insolens,* a strain of Neocallimastix, in particular *Neocallimastix patriciarum,* a strain of Orpinomyces sp., a strain of Penicillium, in particular *Penicillium janthinellum,* a strain of Thermomyces, in particular *Thermomyces lanuginosus* (syn. *Humicola lanuginosa*), or a strain of Trichoderma, in particular *Trichoderma longibrachiatum* and *Trichoderna resii,* or it may be of bacterial origin and may be derived from a strain of Bacillus, in particular *Bacillus circulans, Bacillus pumilus, Bacillus stearothermophilus,* and *Bacillus subtilis,* a strain of *Cellulomonas fimi,* in particular *Cellulomonas fimi,* a strain of Clostridium, in particular *Clostridium thermocellum,* a strain of Dictyoglomus, in particular *Dictyoglomus thermophilum,* a strain of Microtetraspora, in particular *Microtetraspora flexuosa,* a strain of Streptomyces, in particular *Streptomyces lividans,* and *Streptomyces olivochromogenes,* or a strain of Thermomonospora, or it may be of yeast origin and may be derived from a strain of Aureobasidium.

The cellulase enzyme may derived from a strain of Bacterioides, a strain of Cellulomonas, in particular *Cellulomonas fimi,* a strain of Clostridium, in particular *Clostridium thermocellum,* a strain of Erwinia, in particular *Erwinia chrysanthermis,* a strain of Fusarium, in particular *Fusarium oxysporum,* a strain of Humicola, in particular *Humicola insolens* and *Humicola lanuginosa* (syn. *Thermomyces lanuginosus*), a strain of Microbispora, in particular *Microbispora bispora,* a strain of Myceliopthora, in particular *Myceliopthora thermophile,* a strain of Neocallimastix, in particular *Neocallimastix frontalis,* a strain of Piromonas, in particular *Piromonas communis,* a strain of Pseudomonas, a strain of Robillarda, a strain of Ruminococcus, a strain of Sphaeromonas, in particular *Sphaeromonas communis,* a strain of Trichoderrma, in particular *Trichoderma viride, Trichoderma reesei* and *Trichoderma koningii,* or a strain of Thermonospora.

In a more preferred embodiment, an enzyme preparation comprising multiple enzyme activities is employed, e.g., a multi-active β-glucanase preparation produced by a strain of *Humicola insolens.* Such a preparation is commercially available as Ultraflo™, a multi-active β-glucanase preparation produced by *Humicola insolens,* available from Novo Nordisk A/S, Denmark.

In another preferred embodiment a multienzyme complex containing a wide range of carbohydrases including arabanase, cellulase, β-glucanase, hemi-cellulase and xylanase obtained from Aspergillus, is employed. Such a preparation is commercially available as Viscozyme™, available from Novo Nordisk A/S, Denmark.

In yet another preferred embodiment an enzyme preparation obtained by submerged fermentation of *Trichoderma reesei,* is employed. Such a preparation is commercially available as Celluclast™, available from Novo Nordisk A/S, Denmark.

Process Conditions and Equipment

The process of the invention comprises step (i): subjecting the proteinaceous vegetable material to the action of one or more carbohydrate degrading enzyme(s), thereby obtaining a mixture comprising proteins and hydrolyzed carbohydrates; and step (ii): subjecting the mixture of step (i) to a separation process in order to separate the proteins from the hydrolyzed carbohydrates.

Step (i) and step (ii) may be carried out as two subsequent steps, or they may be performed simultaneously. Also the process of the invention may be carried out as a batch process or as a continuous process. If the process of the invention is carried out as a continuous process, step (i) and step (ii) are preferably carried out simultaneously.

The process of the invention may be carried out at process conditions conventionally employed for the isolation and modification of proteins from vegetable sources, using existing equipment, as described in the art [cf. e.g. Olsen H S; Continuous Pilot Plant Production of Bean Protein by Extraction, Centrifugation, Ultrafiltration and Spray Drying; *Lebensm. Wiss. u. Technol.* 1978 11 57–64; and Olsen H S & Adler-Nissen J; Application of Ultra- and Hyperfiltration During Production of Enzymatically Modified Proteins; American Chemical Society Symposium Series, 1981 154 (10) 133–169].

The separation process may be accomplished using any convenient separation technique, in particular membrane separation techniques such as ultrafiltration, diafiltration, microfiltration, nanofiltration, hyperfiltration, etc.

The membrane separation may be accomplished using a membrane having a cut-off value suitable for the protein in question. For many applications, the membrane may have a theoretical molecular weight cut-off of from about 2,000 to about 200,000, more preferred of from about 5,000 to about 150,000, most preferred from about 70,000 to about 100,000.

If step (i) has been accomplished, pH in step (ii) can be in the range of from about 4 to about 9, and the temperature in the range of from about 5 to about 65° C., preferably of from about 50 to about 65° C. If steps (i) and (ii) are carried out simultaneously, pH and temperature must fit the demands of the carbohydrate degrading enzyme employed in step (i).

The process of the invention may be accomplished using carbohydrate degrading enzymes in a dosage normally employed for degrading carbohydrates. It is at resent conteamplated that an enzyme dosage in the range of from about 0.1% to about 10% w/w of enzyme protein of the dry matter composition is suitable.

INDUSTRIAL APPLICATIONS

The protein isolate obtained by the process of the invention may find various industrial applications. The protein isolate is particularly useful for being implemented into products for human or animal nutrition, especially into products for human infants and young animals.

Therefore, in another aspect, the invention provides food products comprising a protein isolate obtained by the process of the invention.

EXAMPLE

The invention is further illustrated in the following example which is not intended to be in any way limiting to the scope of the invention as claimed.

Example 1
Preparation of a Soy Protein Isolate 55 kg of de-fatted soy protein (Unisoy™ 800 from Loders Crooklaan) with high NSI (>70) is added to 305 kg water at 55° C. pH is adjustment to 8.5 during 20 minutes using NaOH.

The mixture is subjected to separation by centrifugation (sludge:supernatant=60:40). The sludge is added water up to initial volume and separated again.

The two supernatants (420 liters, 7.4 Brix) is added 2% Ultraflo™ (from Novo Nordisk A/S, Denmark), based on Brix dry matter=621 g (Ultraflo™ is a multi-activer β-glucabase preparation produced by a selected strain of *Humicola insolens* in which the dominant activities are the cellulase, xylanase, pentosanase and arabanase activities).

The mixture was subjected to ultrafiltration including diafiltration. The equipment used was a PCI Membrane Systems™ mounted with FC 100 membranes (having a theoretical molecular weight cut-off value of 100,000). Concentration and diafiltration were performed at 12–13 Brix.

Flash treatment and spray drying (Tin=200 C., Tout=80 C.).

The end product is a soy protein isolate holding more than 90% w/w of protein of the dry solids, with very high solubility and good organoleptic properties.

Example 2
Preparation of a Soy Protein Isolate

Untoasted de-fatted soy meal with a PSI of 55% at pH 6.5 and water are mixed to a dry matter content of 10% at a temperature of 62–63° C. The pH of the slurry is adjusted to 8.5 with 4N NaOH.

2% Ultraflo™ (from Novo Nordisk A/S, Denmark) based on dry matter is added (Ultraflo™ is a multi-active β-glucabase preparation produced by a selected strain of *Humicola insolens* in which the dominant activities the are cellulase, xylanase, pentosanase and arabanase activities). After 30 minutes holding time the soluble proteins are extracted from the sludge by means of two centrifugation steps whereby an extraction efficiency of approx. 90% is obtained.

After the first centrifugation the sludge is rediluted with deionized water, still at 62–63° C., and passed over the second centrifugation step whereafter the sludge is disposed.

The centrifugate from both centrifugations are collected in the feed tank to the first ultrafiltration unit.

It is preferred that the temperature of the process liquid during mixing, extraction and ultrafiltration 1 is kept above 60° C. in order to limit bacterial growth, and also that the temperature is kept below 64–65° C. during mixing and extraction in order to prevent protein denaturation, excess coloring and degradation of the organoleptic properties.

The centrifugate is ultrafiltered in order to wash out carbohydrates and salts from the protein extract. The centrifugate is concentrated to maximum 5.5% DS and diafiltered by addition of deionized water until $$\%DS(\text{permeate})/\%DS(\text{rententate})=0.09$$

Then the retentate is concentrated to 9–10% DS. The permeate is disposed.

The retentate is pasteurized at 125° C. for 3–4 seconds, to lower the bacterial counts in the product.

The liquid is concentrated and desalinated by nanofiltration at 55° C., on AFC 30 membranes from PCI Membrane Systems. In case low osmolality is desired, diafiltration with addition of deionized water can be performed before the final concentration.

The nanofiltration is stopped at 30° Brix because of low flux.

The protein isolate is spray-dried and agglomerated at Tin 200° C. The water content in the spray-dried powder preferably should be below 6.5% to obtain satisfactory stability of the powder.

What is claimed is:

1. A method of preparing a soy protein isolate or concentrate from a proteinaceous soy material, said method comprising:
   (i) suspending the soy protein-containing material in an aqueous solution at a pH of above 7;
   (ii) subjecting the suspension obtained in (i) to the action of one or more carbohydrate degrading enzyme(s), thereby obtaining a mixture comprising proteins and hydrolyzed carbohydrates; and (iii) subjecting the mixture of step (ii) to a separation process comprising membrane filtration process in order to separate the proteins from the hydrolyzed carbohydrates to obtain as a product a soy protein isolate or concentrate.

2. The method according to claim 1, wherein the carbohydrate degrading enzyme is a glycosidase (EC 3.2).

3. The method according to claim 2, wherein the glycosidase is selected from the group consisting of an amylase, an arabinanase, an arabinofuranosidase, a galactanase, an α-galactosidase, a β-galactosidase, a polygalacturonase, a pectin methyl esterase, a rhamnogalacturonase, a rhamnogalacturon acetyl esterase, a pectin lyase, a xylanase, a cellulase, β-glucosidase, a cellobiohydrolase, a xylosidase, a mannanase, a glucuronisidase, a β-glucanase, and combinations of any of the foregoing.

4. The method according to claim 1, further comprising, prior to step (ii), subjecting the suspension to centrifugation, and recovering the supernatant, wherein the supernatant is used in step (ii).

5. The method according to claim 1, wherein the material is de-fatted soy bean.

6. The method according to claim 1, wherein the membrain filtration is ultrafiltration, diafiltration, or microfiltration.

7. The method according to claim 1, wherein the membrane filtration step is accomplished using a membrane have theoretical molecular weight cut-off of from about 2,000 to about 1,000,000.

8. The method according to claim 7, wherein the membrane filtration step is accomplished using a membrane have a theoretical molecular weight cut-off of from about 2,000 to about 200,000.

9. The method according to claim 1, wherein the enzymes of step (ii) are added in the range of from about 0.1% to about 10% w/w of enzyme protein of the dry matter composition.

10. The method according to claim 1, wherein steps (ii) and (iii) are carried out simultaneously.

11. The method according to claim 1 which is carried out as a continuous process.

12. The method according to claim 1, wherein steps (ii) and (iii) are carried out as two successive steps.

13. The method according to claim 1 which is carried out as a batch process.

14. A soy protein isolate or concentrate obtained by the method according to claim 1.

15. The method according to claim 1, wherein the mixture obtained in step (ii) is subjected to centrifugation to obtain a supernatant, and the supernatant is used in step (iii).

16. The method according to claim 1, wherein the product is a soy protein isolate.

17. A method for the manufacture of a food product, said method comprising incorporating into a food a soy protein isolate or concentrate obtained using the method of claim 1.

18. A method as defined in claim 17, wherein said food product is a food product for consumption by animals.

19. A method as defined in claim 17, wherein said food product is a food product for consumption by humans.

20. A method as defined in claim 19, wherein said food product is a food product for consumption by human infants.

21. A method of isolating proteins from a proteinaceous soy material, said method comprising:

(i) suspending the material in an aqueous solution at a pH of above 7;

(ii) subjecting the suspension obtained in (i) to the action of one or more carbohydrate degrading enzyme(s), thereby obtaining a mixture comprising proteins and hydrolyzed carbohydrates; and (iii) subjecting the mixture of step (ii) to a separation process in order to separate the proteins from the hydrolyzed carbohydrates to obtain a soy protein product, wherein the product comprises more than 80% by dry weight of soy protein.

22. The method according to claim 21, wherein the product comprises more than 90% by dry weight of soy protein.

23. The method according to claim 21, furtherr comprising, prior to step (ii) subjecting the suspension to centrifugation, and recovering the supernatant, wherein the supernatant is used in step (ii).

24. The method according to claim 23, in which the separation process according to step (iii) is accomplished by membrane filtration.

25. The method according to claim 21, wherein the separation in step (iii) comprises centrifugation and recovery of the supernatant; followed by ultrafiltration of the supernatant.

26. The method according to claim 21, wherein the product is a soy protein isolate.

27. A method for the manufacture of a food product, said method comprising incorporating into a food a soy protein isolate or concentrate obtained using the method of claim 21.

28. A method as defined in claim 27, wherein said food product is a food product for consumption by animals.

29. A method as defined in claim 27, wherein said food product is a food product for consumption by humans.

30. A method as defined in claim 18, wherein said food product is a food product for consumption by human infants.

* * * * *